United States Patent
Falla et al.

(10) Patent No.: US 7,045,340 B2
(45) Date of Patent: May 16, 2006

(54) BACTERIAL COMPOSITION, METHOD AND INSTALLATION FOR THE PRE-TREATING EFFLUENTS LOADED WITH ORGANIC FATTY SUBSTANCES

(75) Inventors: Jairo Falla, Metz (FR); Daniel Morabito, Orleans (FR); Gunter Graf, Merzig (DE); Thierry Sensenbrenner, Lingolsheim (FR); Astride Ritter, Strasbourg (FR)

(73) Assignee: Aqua Terra Environnement Holding S.A., Luxembourg (LU)

( * ) Notice: Subject to any disclaimer, the term of this patent is extended or adjusted under 35 U.S.C. 154(b) by 243 days.

(21) Appl. No.: 10/088,596

(22) PCT Filed: Jul. 27, 2001

(86) PCT No.: PCT/FR01/02486

§ 371 (c)(1),
(2), (4) Date: Jun. 10, 2002

(87) PCT Pub. No.: WO02/10078

PCT Pub. Date: Feb. 7, 2002

(65) Prior Publication Data

US 2002/0197707 A1    Dec. 26, 2002

Related U.S. Application Data

(60) Provisional application No. 60/290,049, filed on May 11, 2001.

(30) Foreign Application Priority Data

Jul. 28, 2000   (FR) .................................. 00 10003

(51) Int. Cl.
*C11C 1/00* (2006.01)
(52) U.S. Cl. ...................... 435/271; 435/828; 435/852; 435/880
(58) Field of Classification Search ................ 435/262, 435/267, 271, 852, 880
See application file for complete search history.

(56) References Cited

U.S. PATENT DOCUMENTS

| 5,532,162 A | 7/1996 | Aamot ........................ 435/264 |
| 5,952,188 A | 9/1999 | Kumar et al. ................. 435/14 |

FOREIGN PATENT DOCUMENTS

EP    0 492 426 A1    7/1992

OTHER PUBLICATIONS

XP-001004725, Dilek et al., "Investigation into the Microbiology of a High Rate Jet-Loop Activated Sludge Reator Treating Brewery Wastewater", vol. 34, No. 5-6, pp. 107-112.

*Primary Examiner*—David Redding
(74) *Attorney, Agent, or Firm*—Young & Thompson

(57) ABSTRACT

A bacterial composition, a process and a facility for the pre-treatment of effluent rich in organic fats of animal or vegetable origin. The bacterial composition principally is the bacterial strain *Klebsiella oxytoca*. The process consists of supplying a homogenisation and/or processing vessel (1) with effluent to be pre-treated, as it is produced, activating a recirculation circuit (2) between the vessel and a biological reactor (3) to obtain a fat dilution rate situated between 0.400 h$^{-1}$ and 1.500 h$^{-1}$ for an initial fat concentration of 1 g/l, degrading the fats in the biological reactor (3) using the bacterial composition and discharging the pre-treated effluent to a final treatment unit such as a purification plant.

9 Claims, 2 Drawing Sheets

Figure 1:
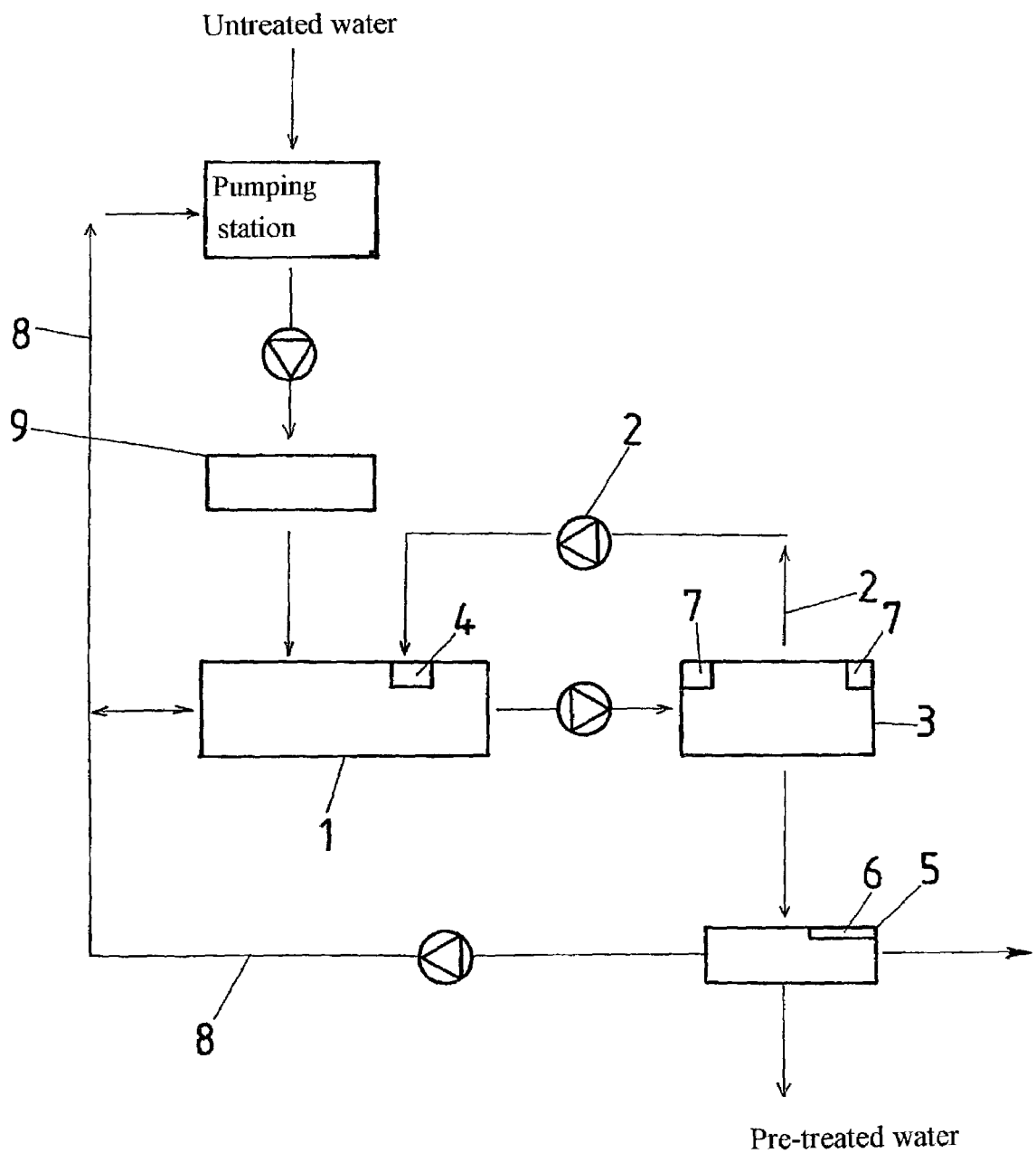

BACTERIAL COMPOSITION, METHOD AND INSTALLATION FOR THE PRE-TREATING EFFLUENTS LOADED WITH ORGANIC FATTY SUBSTANCES

This application is a 371 of PCT/FR01/02486 filed Jul. 27, 2001 which claims benefit of application Ser. No. 60/290,049 filed May 11, 2001.

The present invention relates to the field of the treatment of effluent rich in organic fats of animal or vegetable origin such as result from industrial processes, particularly those implemented in the food and agro-food field or in similar sectors. The invention relates most particularly to the field of the pre-treatment of said effluent and concerns a bacterial composition, a process and a facility for pre-treating the above-mentioned effluent.

The treatment of the residual fats or lipids produced in industry poses a fair number of problems. Indeed, following the health problems encountered in the treatment of animal fats (the so-called "mad cow" disease) and the new policies on environmental matters, requirements in connection with treatments of this type of waste have become ever more restrictive, both technically (bringing treatment a facility up to standard, improving output, etc.) and in terms of cost.

In addition, existing treatment capacities, for example at communal purification plants, are often inadequate, particularly when the level of fats present in the effluent to be treated is high.

To try to resolve the problems connected with the treatment of fatty effluent produced in large quantities, various solutions have already been considered and some have been implemented.

Thus, it has been proposed in particular to spread said effluent directly over large areas of agricultural land and in this way distribute the impact of dumping them on the environment, so as to achieve acceptable levels of surface pollution.

Another solution consists of storing said fats, possibly after concentration and/or special processing in an approved dumping facility with a view to final treatment in a specialised centre or incineration unit.

Another route followed is composting the fats.

However, faced with the ever-increasing quantities of fatty effluent produced, these solutions cannot be satisfactory in the medium- or long-term, particularly in view of the strengthening of present anti-pollution regulations which mean or will mean that these processes do not comply and/or are not economically viable.

Proposals have also been made to adapt conventional purification plants by incorporating fat separators (static separators or with air injection) or saponification techniques for the special treatment of this type of effluent.

However, this adaptation would cause costly over-sizing of said plants to allow them to respond to the quantities of pollutants generated, without however providing reliable control of changes in the level of pollution, and therefore of the quality of the final effluent discharged, mainly due to the continuous operation of these installations.

Finally, several processes for the biological treatment of fats are known in which the effluents to be treated are put in contact with special bio-additives and/or a suitable purifying biomass that degrades the fats by transforming them into gas and sludge. These processes can be implemented aerobically or anaerobically.

However, the lactic acid bacteria employed in the processes used at present do not allow complete hydrolysis of long-chain fatty acids, and this causes a damaging overload of organic matter in the aeration tank.

Moreover, the bacteria used at present do not retain, as they multiply, the properties initially conferred on them when they were created by genetic manipulation. Frequent and costly inputs of new bacteria are therefore necessary to maintain the effectiveness of the process.

Consequently, the problem posed for the present invention consists of reducing the above-mentioned drawbacks and designing a bacterial composition, a process and a facility for the pre-treatment of effluent rich in fats, more especially effluent from the food and agro-food field, that provide a more effective solution (output in terms of fats eliminated of over 90%), that are inexpensive and more reliable over time, and that allow the strictest regulatory requirements with regard to the purified effluent discharged to be met.

To this end, the present invention relates to a bacterial composition for the degradation of organic fats, characterised in that it comprises principally the bacterial strain *Klebsiella oxytoca*, and the use of a bacterial composition according to the present invention for the treatment or pre-treatment of effluent rich in organic fats, particularly effluent from the food or agro-food industry.

The present invention also relates to a process for the pre-treatment of effluent rich in organic fats, particularly effluent from the food and agro-food industry, characterised in that it consists of directly pre-treating said effluent containing said fats when it leaves the place of production and in that it consists of accomplishing the following stages:

supplying a homogenisation and/or processing vessel with effluent to be pre-treated, as it is produced and activating a recirculation circuit between this vessel and a biological reactor so as to obtain in said biological reactor a rate of fat dilution inversely proportional to the fat concentration initially present in the effluent to be pre-treated, situated between $0.400\ h^{-1}$ and $1.500\ h^{-1}$ for a fat concentration contained in said effluent to be pre-treated entering the homogenisation and/or processing vessel of 1 g/l, degrading said fats in said biological reactor using a bacterial composition according to the present invention, and discharging the pre-treated effluent, now containing practically no fats, to a final treatment unit such as a purification plant.

Finally, the present invention also relates to a facility for the pre-treatment of effluent rich in organic fats, notably for the implementation of the process according to the present invention, characterised in that it consists principally of at least one homogenisation and/or processing vessel, at least one biological reactor of a capacity suited to the daily output of effluent to be pre-treated and the fat concentration in that effluent, said biological reactor being connected to the homogenisation and processing vessel(s) by a recirculation circuit, at least one device for the controlled supply of oxygen arranged in the biological reactor(s) and at least one means of discharging the pre-treated effluent, for example by overflow, outside said biological reactor(s).

Figure 2:
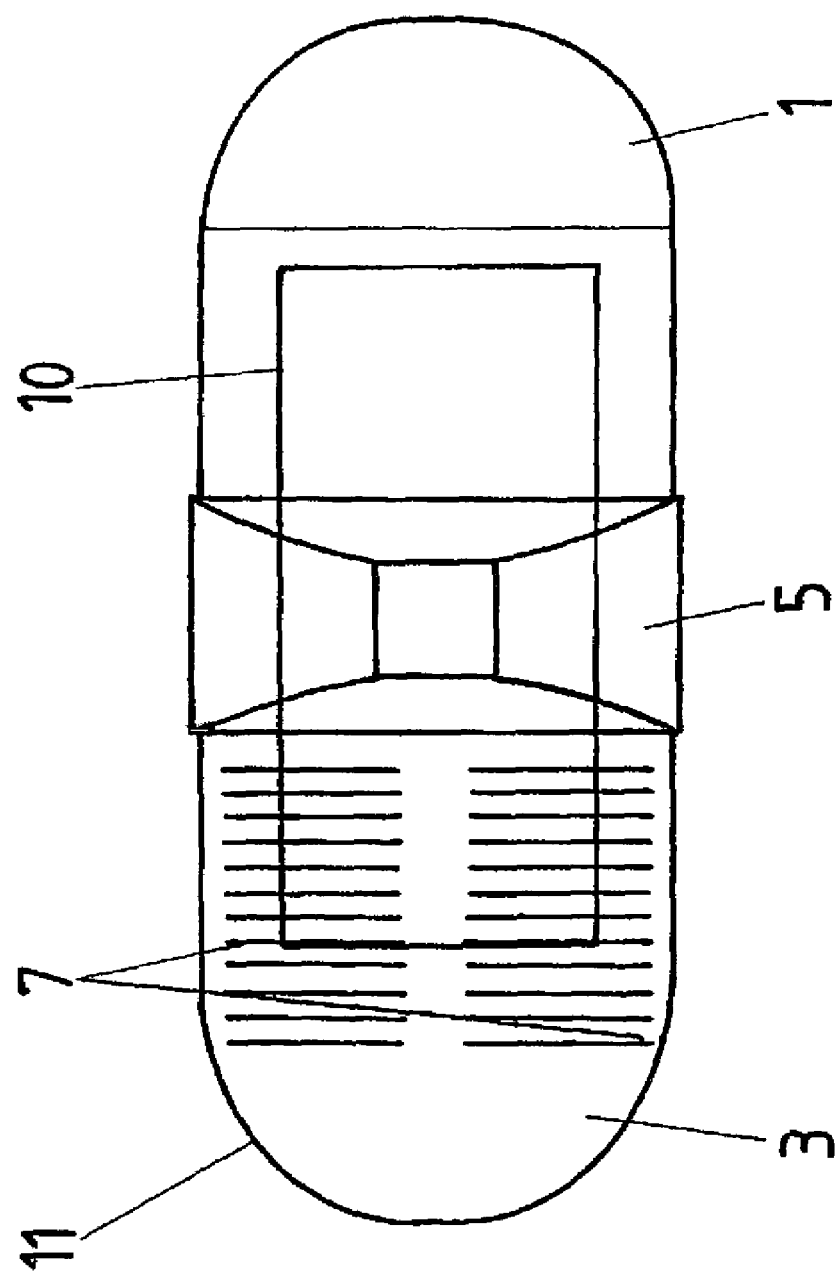

The invention will be better understood by referring to the description below, which relates to a preferred embodiment, given as a non-limiting example, and explained with reference to the accompanying diagrammatic drawings, in which:

FIG. 1 is a simplified diagrammatic outline of the process according to the invention, and FIG. 2 is a simplified view from above of a facility according to the present invention.

In accordance with the present invention, the bacterial composition for degrading organic fats is characterised in that it comprises principally the bacterial strain *Klebsiella oxytoca*. It has unexpectedly and surprisingly been found that the selected strain is particularly effective in the degradation of organic fats, in particular in the degradation of fats of animal or vegetable origin from the food or agro-food industry.

Some non-limiting examples of fats that can be treated by bacteria according to the present invention are fats from pork butchers, butchers, caterers, restaurants, communal catering facilities, animal quartering companies, abattoirs, etc.

According to a first embodiment, the bacterial composition according to the present invention is characterised in that it also comprises the bacterial strain *Serratia odorifera* and/or *Aeromonas hydrophyla*.

Surprisingly and unexpectedly, the specific association of these bacterial strains proved to be particularly effective and economic in the degradation of the aforementioned fats. The strains according to the invention therefore provide excellent output in terms of degraded fats.

In practice, the micro-organism(s) according to the invention are advantageously added in a solid lyophilised form into the culture medium contained in the fat treatment reactor.

As an indication, the average bacterial quantity contained in the composition according to the present invention is of the order of $10^{16}$ bacteria/g of solid matter. When the micro-organisms are seeded, an average quantity of $2.10^{15}$ bacteria/m$^3$ is necessary for the proper effectiveness of said micro-organisms.

Growth conditions for the strains *Klebsiella oxytoca*, *Serratia odorifera* and *Aeromonas hydrophyla* have also been studied. Unexpectedly and surprisingly, it was noted that the aforementioned strains develop particularly well in aerobic conditions, in a wide range of temperatures situated preferably between 15° C. and 40° C., and for a huge range of pH encompassing both slightly acid (pH=5) and slightly alkaline (pH=9) environments, and this permits easier and more effective use of the cultures in question. The very robust nature of these bacteria also guarantees good development and optimal longevity, and therefore high and stable performance over time.

Preferably, the bacterial composition according to the present invention is characterised in that it is composed of:
60% to 90%, preferably about 80% by weight of bacteria of the strain *Klebsiella oxytoca*,
5% to 20%, preferably about 10% by weight of bacteria of the strain *Serratia odorifera*, and
5% to 20%, preferably about 10% by weight of bacteria of the strain *Aeromonas hydrophyla*, the total of the three strains being equal to 100%.

In this way, a mixture of bacteria is obtained that is not only very effective in terms of fat degradation (cf. table below) but also has practical implementation advantages, such as, for example, reduced costs, good longevity, easy conditions for culture, elimination, recycling, etc.

The aforementioned bacterial strains initialise fat degradation by cutting the ester bond between the glycerol and long fatty acid chains since they contain lipases that allow this enzymatic cutting to operate. Degradation ($\square$-oxidation) of the fatty acids follows based on the free carboxyl group by decarbonation of an acyl group. This final stage is also accomplished by these strains.

Thus, the bacterial composition according to the present invention can be used for the treatment or pre-treatment of effluent rich in organic fats, particularly effluent from the food or agro-food industry.

Reference will now be made to FIG. 1 which illustrates diagrammatically the process of the present invention. Said process is characterised in that it consists of pre-treating directly said effluent containing said fats as it leaves the place of production and in that it consists of accomplishing the following stages:
supplying a homogenisation and/or processing vessel 1 with effluent to be pre-treated, as it is produced and activating a recirculation circuit 2 between this vessel and a biological reactor 3 so as to obtain in said biological reactor 3 a rate of fat dilution inversely proportional to the fat concentration initially present in the effluent to be pre-treated, situated between 0.400 h$^{-1}$ and 1.500 h$^{-1}$ for a concentration of fats contained in said effluent to be pre-treated entering the homogenisation and/or processing vessel 1 of 1 g/l,
degrading said fats in said biological reactor 3 using a bacterial composition according to the present invention, and
discharging the pre-treated effluent, now containing practically no fats, to a final treatment unit such as a purification plant.

The process according to the present invention allows work to be done directly on the flow of fat-rich effluent, in other words with no prior physico-chemical separation. Of course, it is also possible to work on fats that have undergone prior physical treatment.

Degradation of fats by hydrolysis and oxidation is accomplished using the bacterial composition according to the present invention. This composition is particularly effective when the fatty effluent is supplied continuously. This is why biodegradation of fats is effected directly on the untreated effluent, working on the flow.

The effectiveness of said composition depends on the dilution rate at the facility. This dilution rate corresponds to the ratio between the effluent output and the volume of the biological reactor 3 and depends on the fat concentration initially present in the effluent to be pre-treated.

According to another advantageous characteristic of the invention, the process according to the present invention is characterised in that the rate of dilution obtained in the biological reactor 3 is inversely proportional to the fat concentration initially present in the effluent to be pre-treated and is situated preferably between 0.528 h$^{-1}$ and 1.056 h$^{-1}$ for a concentration of fats contained in said effluent to be pre-treated entering the homogenisation and/or processing vessel 1 of 1 g/l.

Since the dilution rate is inversely proportional to the concentration of fats initially present in the effluent to be pre-treated, each of the limit values of the rate ranges indicated above (given for a fat concentration of 1 g/l) need only be divided by the appropriate factor to determine the ranges of dilution rates to be used for other concentrations of fats. Thus, for an initial concentration of fats of 0.5 g/l, the dilution rate will be between 0.800 h$^{-1}$ and 3.000 h$^{-1}$, preferably between 1.056 h$^{-1}$ and 2.112 h$^{-1}$, while for an initial fats content of, for example, 4 g/l, said dilution rate will be between 0.100 h$^{-1}$ and 0.375 h$^{-1}$, preferably between 0.132 h$^{-1}$ and 0.264 h$^{-1}$, etc.

Advantageously, the process in accordance with the present invention is characterised in that the fat concentration in the effluent to be pre-treated entering the homogenisation and/or processing vessel 1 is less than 40 g/l, and preferably situated between 0.5 g/l and 10 g/l. In fact, too low a fat concentration is likely to damage the proper development (growth) or live preservation of the cultures of micro-organisms, and therefore the chemical performance and economic profitability of the process, and similarly too high a fat concentration may also inhibit bacterial growth.

If the supply of fatty effluent to be treated is not continuous, correct degradation of lipids (in other words an output of the order of 70 to 99%) is generally achieved in 30 to 40 hours.

In continuous mode, as previously indicated, the dilution rate of fats initially present in the effluent to be pretreated must be between $0.400\,h^{-1}$ and $1.500\,h^{-1}$ for a concentration of fats contained in said effluent to be pre-treated entering the homogenisation and/or processing vessel 1 of 1 g/liter. Outside this range of dilution rate values, it is possible that the lipid degradation activity may reduce significantly.

According to a variant, the effluent to be pre-treated may also be subjected to a prior screening operation 9 with a view to separating any solid matter present in said effluent, before said effluent reaches the homogenisation and/or processing vessel 1. This measure allows the size of solid particles poured into said homogenisation and/or processing vessel 1 to be limited, by trapping, for example, solid particles with sections of more than 1 cm².

The homogenisation and/or processing vessel 1 is equipped with an agitator or any other means of agitation normally used in these applications that permits good mixing and therefore good homogenisation of the effluent (temperature, pH, fat concentration, etc.). Advantageously, the effluent arrives from above into said vessel 1, and this allows the biomass to be well dispersed.

From said homogenisation and/or processing vessel 1, the effluent is pumped at an output that depends on the above-mentioned dilution rate and thus the fat concentration, towards the biological reactor 3. This reactor is equipped with an aeration device and a pump (not illustrated) that allows the recirculation circuit 2 between said biological reactor 3 and said homogenisation and/or processing vessel 1 to be activated.

In a particularly advantageous variation, illustrated in FIG. 2, the arrival in the homogenisation and/or processing vessel 1 of the recirculation water discharged by the recirculation circuit 2 is effected from above by a spraying device 4. In this way, the potential formation of a layer of fat on the surface of said homogenisation and/or processing vessel 1 is avoided.

Biological degradation occurs principally in the biological reactor 3 due to oxygen enrichment of the medium, for example by using an aeration or oxygenation device, preferably using at least one device for providing a controlled supply of oxygen 7.

In fact, the quantity of air to be injected into the biological reactor 3 must be sufficiently large for development of the biomass to occur but must not cause fats to float in said biological reactor 3. Air is introduced preferably by coarse bubbling.

From the biological reactor 3, the pre-treated effluent overflows and runs by gravity into a decanter 5 where the particles that can be decanted form a sediment. According to a preferred embodiment, the pre-treated effluent is discharged by means of a decanter 5 over the upper part of which a floating pump 6 is provided to expel surface floating sludge that cannot be decanted.

The decanter 5 is preferably cone-shaped at the base and the pre-treated water similarly runs off by overflow.

The following table gives examples of results obtained when implementing the process for effluent originating from various industrial sectors:

|  | Effluent from a caterer | | | Effluent from a pork butcher | | | Effluent from poultry abattoir | | | Fat from production of a animal feedstuffs | | |
| --- | --- | --- | --- | --- | --- | --- | --- | --- | --- | --- | --- | --- |
|  | UW g/l | PTW g/l | O % | UW g/l | PTW g/l | O % | UW g/l | PTW g/l | O % | UW g/l | PTW g/l | O % |
| Fat conc. | 3.00 | 0.15 | 95 | 2.60 | 0.10 | 96 | 0.65 | 0.12 | 82 | 56.06 | 3.18 | 95 |
| COD | 3.73 | 1.12 | 70 | 1.86 | 1.10 | 41 | 4.52 | 1.64 | 64 | 93.30 | 8.69 | 91 |
| BOD$_5$ | 1.14 | 0.51 | 55 |  |  |  | 2.45 | 0.82 | 67 |  |  |  |
| TMS | 1.38 | 0.61 | 56 | 1.55 | 0.28 | 82 | 1.60 | 0.54 | 66 | 76.43 | 4.96 | 94 |

UW = untreated water, PTW-pre-treated water, O = output
COD = chemical oxygen demand
BOD$_5$ = biochemical oxygen demand after 5 days
TMS = total matter in suspension The average time effluent remains in the facility according to the invention is of the order of 24 hours.

To further increase the output of the process, surface floating sludge that cannot be decanted may be reinjected into, or upstream of, the homogenisation and/or processing vessel 1, for example by means of the recycling circuit 8 illustrated diagrammatically in FIG. 1. The excess sludge that can be decanted is discharged.

The present invention also relates to a facility for pre-treating effluent rich in organic fats, and is intended particularly, but not restrictively, for implementation of the pre-treatment process described above.

This facility consists principally, as is shown in FIG. 2 of the accompanying drawings, of at least one homogenisation and/or processing vessel 1, at least one biological reactor 3 of a capacity suited to the daily output of effluent to be pre-treated and its fat concentration, said biological reactor 3 being connected to the homogenisation and/or processing vessel(s) 1 by a recirculation circuit 2, at least one device for providing a controlled supply of oxygen 7 arranged in the biological reactor(s) 3 and at least one means of discharging the pre-treated effluent, for example by overflow, outside said biological reactor(s) 3. For reasons of clarity, the recirculation circuit 2 has not been illustrated in FIG. 2.

Advantageously, the biological reactor 3 is configured to facilitate extraction of the residual sludge by the decanter 5, and to render it suitable to receive at least one device for providing a controlled supply of oxygen 7 which, by supplying a large injection of oxygen, permits maintenance or acceleration of the development and activity of bacterial biodegradation in order to bring biological pollution rapidly to an acceptable level for final treatment, for example in a purification plant.

The biological reactor 3 may be arranged inside a storage tank, enclosing the device for providing a controlled supply of oxygen 7, for example a small bubble diffuser, and may be provided with traditional means of injecting chemical and/or biological products to promote purification. It is also advantageously equipped with the usual means of analysis and quality control of effluent before and/or after treatment, notably of its degree of fat pollution and/or level of oxygenation. These means of analysis and other technical devices (pumps, generators, valves, control panel, etc.) are preferably arranged together in a technical installation 10.

Said biological reactor 3 may, for example consist of a reactor of the type manufactured by the applicant. The residual sludge obtained after extraction of the liquid effluent comprises firstly, suspended matter that can be decanted and is not easily biodegraded and secondly, surface floating sludge that cannot be decanted which can be reinjected into or upstream of the homogenisation and/or processing vessel 1 by an appropriate recycling circuit 8.

Sludge that can be decanted may be discharged, with a view to storing or spreading it. The final sludge may also, depending on the quantities produced and the capacity of the decanter 5, remain stored in said decanter 5 for complete extraction and cleaning every 1 to 2 years, for example.

In order to eliminate large solid particles and limit the amount of matter to be decanted, provision may advantageously be made for the effluent to be sieved or screened 9, possibly in association with decanting, before being poured into the homogenisation and/or processing vessel 1. In this case, the necessary equipment, known per se, may be added to the facility.

Advantageously, the facility according to the invention is collected together in an oval vessel 11, preferably, made of concrete and compartmented into three tanks, which may be buried or half-buried, the machinery being collected together in a technical installation 10 placed above said oval vessel.

The facility according to the invention may also comprise at least one process control and management unit, for example of the programmable controller type, which automatically controls the progress of the successive stages of treatment, by being linked to suitable sensors and actuators.

In the case of effluent from the food industry, for example, from an average pie production unit, the quantities of fats treated may be of the order of a tonne of fat per day, which corresponds to 35 m³ per day of discharge at about 5 g/l of fats.

Of course, the invention is not limited to the embodiment described and illustrated in the accompanying drawings. Modifications are possible, particularly from the point of view of the composition of the various elements or by substitution of technical equivalents, without however departing from the scope of protection of the invention.

The invention claimed is:

1. A bacterial composition for the degradation of organic fats, comprising bacterial strains *Klebsiella oxytoca, Serratia odorifera*, and *Aeromonas hydrophyla*.

2. The composition according to claim 1, wherein the bacterial composition comprises 60% to 90% of the strain *Klebsiella oxytoca*, 5% to 20% of the bacteria strain *Serratia odorifera*, and 5% to 20% of the bacteria strain *Aeromonas hydrophyla*, the total of the three strains being equal to 100%.

3. A method for the treatment or pretreatment of effluent rich in organic fats, comprising adding the bacterial composition according to claim 1 to said effluent.

4. A process for the pre-treatment of effluent rich in organic fats comprising:
   supplying a homogenisation and/or processing vessel (1) with effluent as the effluent is produced;
   activating a recirculation circuit (2) between the vessel and a biological reactor (3) so as to obtain a dilution rate wherein the fats are inversely proportional to the fat concentration initially present in the effluent at a rate between 0.400 $h^{-1}$ and 1.500 $h^{-1}$ so that a fat concentration contained in the effluent enters the homogenisation and/or processing vessel (1) is less than 40 g/l;
   degrading the fats in the biological reactor (3) using a bacterial composition according to claim 1; and
   discharging an effluent, now containing practically no fats, to a final treatment unit.

5. The process according to claim 4, wherein the dilution rate obtained in the biological reactor (3) is inversely proportional to the fat concentration initially present in the effluent to be pre-treated and situated between 0.528 $h^{-1}$ and 1.056 $h^{-1}$ so that the fat concentration contained in the effluent enters the homogenisation and/or processing vessel (1) at 1 g/l.

6. The process according to claim 4, wherein the fat concentration of the pre-treated effluent entering the homogenisation and/or processing vessel (1) is less than between 0.5–10.0 g/l.

7. The process according to claim 4, wherein the arrival in the homogenisation and/or processing vessel (1) of the recirculation water discharged by the recirculation circuit (2) is effected from above by a spraying device (4).

8. The process according to claim 4, wherein the pre-treated effluent is discharged using a decanter (5) on the upper part of which a floating pump (6) is provided for the elimination of surface floating sludge that cannot be decanted.

9. The process according to claim 8, wherein the surface floating sludge that cannot be decanted is reinjected into, or upstream of the homogenisation and/or processing vessel (1).

* * * * *